(12) United States Patent
Huang et al.

(10) Patent No.: US 10,983,107 B2
(45) Date of Patent: Apr. 20, 2021

(54) SYSTEMS AND METHODS FOR CONTROLLING BI-DIRECTIONAL FORCES FOR CLOT ASSESSMENT

(71) Applicant: Medtronic Vascular, Inc., Santa Rosa, CA (US)

(72) Inventors: Trevor Huang, Maple Grove, MN (US); Charlene Yuan, Plymouth, MN (US); Tessy Kanayinkal, Maple Grove, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 203 days.

(21) Appl. No.: 16/110,179

(22) Filed: Aug. 23, 2018

(65) Prior Publication Data

US 2019/0064142 A1    Feb. 28, 2019

Related U.S. Application Data

(60) Provisional application No. 62/549,248, filed on Aug. 23, 2017.

(51) Int. Cl.
  *G01N 33/49*   (2006.01)
  *G01N 11/00*   (2006.01)
  *G01N 11/12*   (2006.01)
  *G01N 11/16*   (2006.01)

(52) U.S. Cl.
  CPC .............. *G01N 33/49* (2013.01); *G01N 11/00* (2013.01); *G01N 11/12* (2013.01); *G01N 11/16* (2013.01); *G01N 33/4905* (2013.01)

(58) Field of Classification Search
  CPC .... G01N 33/49; G01N 11/00; G01N 33/4905; G01N 11/12; G01N 11/16
  See application file for complete search history.

(56) References Cited

U.S. PATENT DOCUMENTS

| | | | |
|---|---|---|---|
| 5,629,209 A | 5/1997 | Braun, Sr. et al. | |
| 6,613,286 B2 | 9/2003 | Braun, Sr. et al. | |
| 8,460,938 B2 | 6/2013 | Forsell | |
| 2005/0233460 A1* | 10/2005 | Clague | G01N 11/162 436/69 |
| 2005/0233466 A1* | 10/2005 | Wright | G01N 33/4905 436/165 |

(Continued)

OTHER PUBLICATIONS

PCT International Search Report and Written Opinion dated Dec. 14, 2018 in corresponding PCT Appln.No. PCT/US2018/047764.

*Primary Examiner* — Samuel P Siefke
(74) *Attorney, Agent, or Firm* — Dicke, Billig & Czaja, PLLC

(57) ABSTRACT

Systems and methods to analyze blood or other fluid sample. The systems and methods utilize bi-directional magnetic forces to push or pull a magnetic object along a post in a chamber housing the fluid sample both before and after clot initiation has been implicated. The magnetic object can be threadably connected to the post. In other embodiments, the chamber is configured such that the magnetic object does not rotate but only slides along the post. Once a clot has been detected, the washer can be moved either up or down to apply either compressive force or strain within the clot, as desired, to evaluate elastic properties or firmness of the clot.

7 Claims, 12 Drawing Sheets

(56) References Cited

U.S. PATENT DOCUMENTS

| | | | |
|---|---|---|---|
| 2014/0273249 A1* | 9/2014 | Yuan | G01N 33/86 436/69 |
| 2014/0315228 A1* | 10/2014 | Yuan | G01N 33/86 435/13 |
| 2018/0172665 A1* | 6/2018 | Yuan | G01N 33/4905 |

* cited by examiner

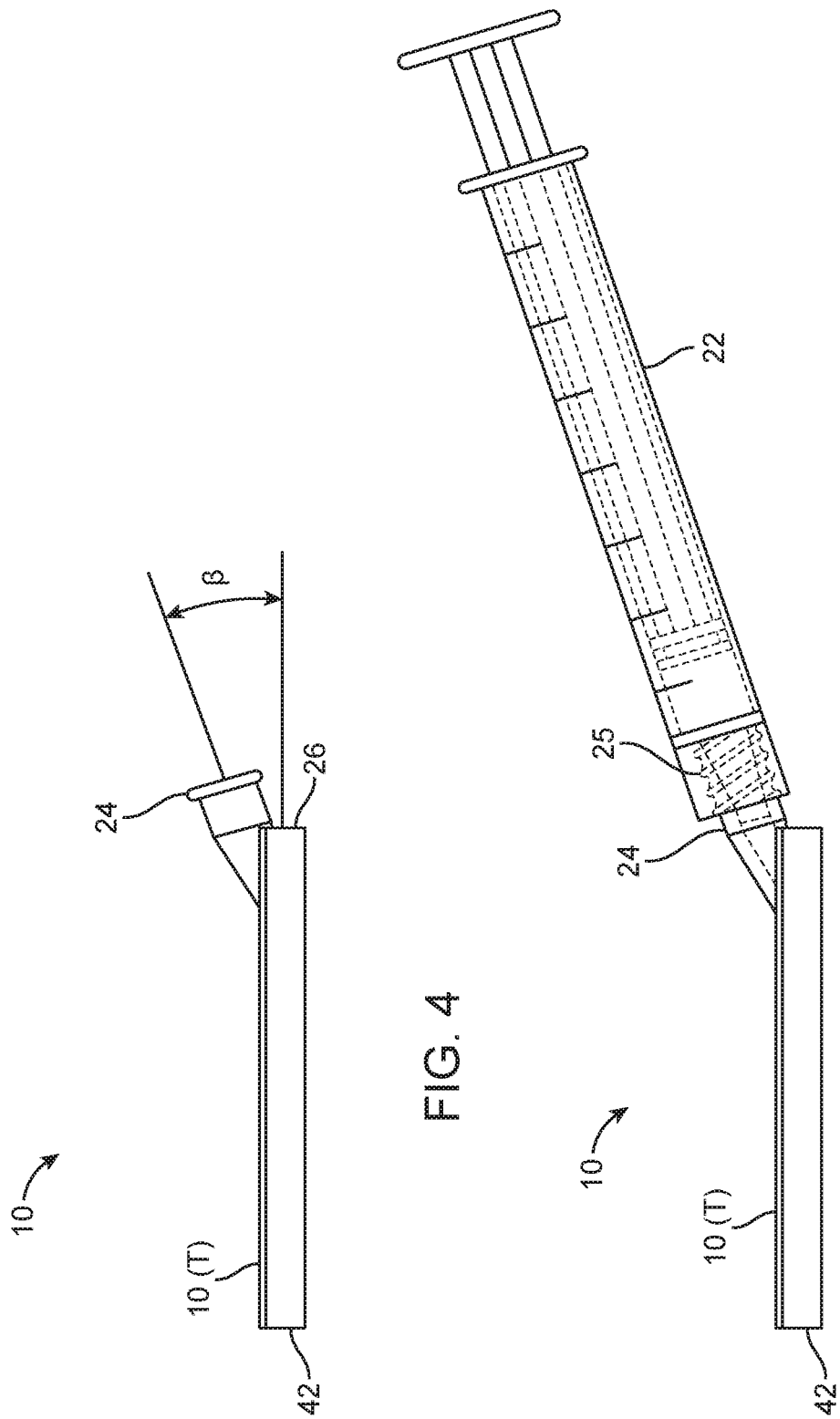

SYSTEMS AND METHODS FOR CONTROLLING BI-DIRECTIONAL FORCES FOR CLOT ASSESSMENT

CROSS-REFERENCE TO RELATED APPLICATIONS

This Non-Provisional patent application claims the benefit of the filing date of U.S. Provisional Patent Application Ser. No. 62/549,248, filed Aug. 23, 2017, the entire teachings of which are incorporated herein by reference.

BACKGROUND

The present disclosure relates to systems and methods of detecting and assessing changes in viscosity and viscoelasticity of a fluid sample (e.g., human blood) during a clot test.

The ability to detect changes in a property of a liquid that has been placed under the influence of a reagent that is capable of changing that property has great practical value. Changes in viscosity, translucence, color, electrical conductivity, optical density, chemical component concentration, and many other properties have been used in a wide variety of tests. For example, detection of changes in the viscosity of liquids such as blood, food products, and various other liquid compositions (e.g., industrial fluids, oil well injection fluids, etc.) form the basis of many very practical tests.

Indeed, the ability to detect changes in the viscosity of human blood can even have life and death consequences. This follows from the fact that a proper balance between normal hemostasis and coagulation or anticoagulation is absolutely essential in maintaining the integrity of the human circulatory system—and in stopping both external and internal bleeding. It is, however, sometimes necessary to modify the natural coagulation system, either by increasing or decreasing the rate of blood coagulation. During open heart surgery for example, a patient is usually supported by a heart/lung bypass machine that provides extracorporeal blood circulation while the heart is stopped. To prevent blood from clotting upon exposure to the bypass system, the patient is treated with high doses of heparin, a naturally occurring substance that significantly prolongs the clotting time of blood. When the time comes to remove the patient from the heart/lung bypass machine, however, it is desirable for the patient's blood to regain its normal coagulation characteristics so that it will again be able to clot and assist in healing incisions and stopping internal or external bleeding. This reversal of the effects of heparin is achieved by treating the patient's blood with an anticoagulant-reversing substance (e.g., protamine) capable of neutralizing heparin or other anticoagulating substances.

To successfully maintain anticoagulation during a surgical procedure, and neutralize the heparin at the conclusion of surgery, it is highly desirable to be able to quickly and accurately determine the concentration of heparin in the patient's blood. Unfortunately, since the activity of heparin varies significantly from batch to batch, and from patient to patient, these determinations cannot be made simply on the basis of the amount of heparin administered. Protamine also varies in potency from batch to batch and from patient to patient. Furthermore, protamine itself can act as an anticoagulant. Thus, for optimal reversal of a given heparin action, it is essential to use only that amount of protamine that will directly neutralize the amount of active heparin in a particular patient's blood.

Such reversals of a heparin action are detected by dose-response tests which measure changes in blood clotting time in response to differing doses of anticoagulant in order to determine the correct dose of anticoagulant for a particular patient. Clotting time or activated clotting time tests are used to determine whether a patient's blood has achieved the desired level of anticoagulation. Heparin/protamine (anticoagulant/neutralizer) titration tests have been developed to provide accurate determinations of heparin (anticoagulant) levels. Such tests are based on measuring the time necessary for the blood to coagulate. Consequently, these titration tests measure coagulation time as an empirical measure of blood viscosity.

Optimal hemostasis management in cardiac surgery not only requires careful dosing and monitoring of anticoagulant, such as heparin, it is also important to monitor platelet function and other clotting factors, such as fibrinogen. Platelet dysfunction is believed to be the primary cause of excessive microvascular bleed following cardiopulmonary bypass surgery. Activated platelet exert contractile force, when allowed to interact with polymerizing fibrin, they significantly increase its tensile strength. While the measurement of clotting time can be achieved by measuring blood viscosity change, the measurement of blood clot tensile strength change is best achieved by blood elasticity change.

By way of example only, U.S. Pat. No. 5,629,209 to Braun, Sr. et al. ("the '209 patent") discloses apparatus and methods for detecting changes in human blood viscosity through use of cartridges that, in conjunction with a test apparatus, are used to detect changes in blood viscosity. Heparinized blood is introduced into the cartridge through an injection port and fills the blood receiving/dispensing reservoir. The blood then moves from the reservoir through at least one conduit into at least one blood-receiving test chamber where it is subjected to a viscosity test. In this test, a freely movable ferromagnetic object is placed within the blood-receiving test chamber. The ferromagnetic object is moved up by an electromagnet in the test apparatus and falls via gravitational pull. Changes in the viscosity of the blood through which the ferromagnetic object falls are detected by determining the position of the ferromagnetic object in the blood-receiving test chamber over a given time period or a given number of rises and falls of the ferromagnetic object. The incoming blood sample can be mixed with a blood viscosity altering agent (e.g., protamine) as it passes through the conduit to the blood-receiving test chamber. Any air in the fluid communication system in front of the incoming blood sample is vented through an air vent/fluid plug device. In addition, U.S. Pat. No. 6,613,286 to Braun, Sr. et al. discloses a related apparatus having constructed passages for increasing the velocity of the fluid flow though said constricted passage and thereby more thoroughly mixing the liquid (blood) and a reagent.

The present disclosure provides improvements generally related to the above.

SUMMARY

Systems and methods of the present disclosure can be used in virtually any test where a reagent is mixed with a liquid sample and then tested for some change in a property of the resulting liquid/reagent mixture. Disclosed systems and methods are particularly well suited for clotting time tests, dose-response tests, and especially titration tests on human blood taken from patients undergoing anticoagulation therapy during heart/lung bypass surgery.

One example of a test procedure commences when a liquid sample to be tested is introduced, under pressure, into a cartridge containing one or more test chambers in which a low-carbon ferromagnetic washer is positioned over a post for mixing test samples and assay reagent and also for sensing the blood viscoelasticity change during the clotting process. Clot detection can be accomplished, for example, by inserting the cartridge into a device and assessing a viscosity change of the sample through lifting of the washer via magnetic lifting force and dropping of the washer and allowing it to fall via gravity. There are some drawbacks, however, to devices that are only capable of actively lifting the washer.

During a test, blood clots can form at any location between a floor and a ceiling of a test chamber. When a clot forms above the washer, the washer can be actively moved up using the device described above by applying the magnetic lifting force to apply compression. It is noted, however, that since the magnetic force is dependent on the gap between the magnet and the washer, and greater lifting force is applied to compress the clot between the washer and the test chamber top and stretch the clot between the washer and the bottom of the test chamber when the washer is closer to the magnet that, therefore, the stress force in a strain-stress elasticity measurement of the clot in this method is not controlled. The strain (compression or stretching) of the clot is not controlled either because the washer initial location at the time of clot formation is not controlled, the distance the washer to be moved up is not controlled. Because neither strain nor stress forces are controlled in the system, the elasticity of the blood clot cannot be reproducibly measured. In the case of a clot formed under the washer, the passive gravity force of the washer on top of the clot would not allow the washer to drop further until the clot starts to retract, which does not occur until later (typically at least about 15 minutes after initiation of the clot test) in the blood hemostasis process. In view of the above, the present inventors recognized that in order for a platelet function test to be able to assess platelet strength and function via clot elasticity measurements, it is desirable for a test device or machine of the system to be able to measure clot elasticity with controlled stress force or strain distance and that actively controlled bi-directional forces can achieve controlled strain and stress forces applied to the clot. The bi-directional forces on a washer can be provided, for example, by utilizing a magnetic washer that can be controlled with an actuating magnet in two directions, by selectively aligning the poles of the magnetic washer with the poles of the actuating magnet to either push or pull the magnetic washer along the post. The position of the washer can be measured with a position sensor. In this way, stress or strain can be applied to the clot for use in measuring viscoelasticity of the clot. In one embodiment, the actuating magnet is a horseshoe magnet that can rotate about its center axis to apply bi-directional forces to the magnetic washer. Similarly, in other embodiments, the actuating magnet is an electromagnet and the polarity of the electromagnet can change as the current reverses direction every half cycle (AC voltage or current source) to apply bi-directional forces to the magnetic washer.

BRIEF DESCRIPTION OF THE DRAWINGS

FIG. 4 is a side view of the cartridge shown in FIG. 2.

FIG. 5 is a side view of the cartridge shown in FIG. 2 with a syringe attached to t cartridge.

DETAILED DESCRIPTION

Figure 1:
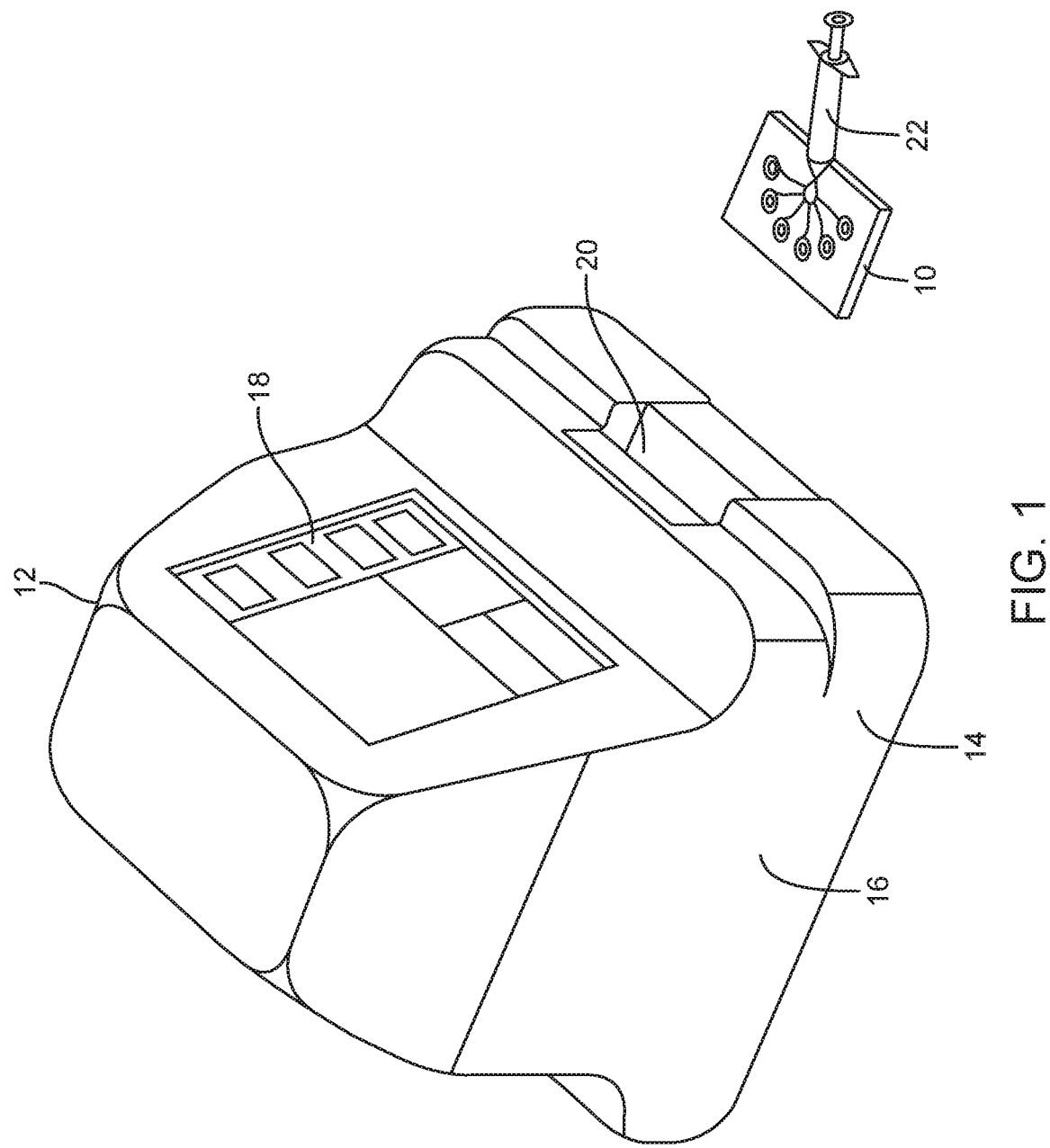
FIG. 1 is a perspective view of a cartridge and a test machine in which the cartridge is inserted.

By way of background, FIG. 1 depicts one example of a disposable cartridge 10 conceptually associated with a machine 12 for testing some property of a liquid that is mixed with a reagent. The machine 12 can be provided with one or more sensor devices (known to those skilled in the test machine manufacturing arts), for detecting various properties of a given liquid/reagent sample. For example, the one or more sensing devices can be used to detect the viscosity, translucence, color, optical density, electrical conductivity, magnetic properties, fluid component concentrations, electromagnetic response, etc. of a sample (or an object placed in the sample e.g., the ferromagnetic washer shown in FIGS. 9, 10 and 14). That is to say that in some of the example embodiments of this disclosure, the machine 12 will be provided with more than one kind of sensing devices so that the machine 12 can simultaneously (or sequentially) detect more than one property of the sample being tested. Such a machine 12 will generally comprises a base 14 and an upper portion 16. The upper portion 16 can include a display device 18 (including a touch-sensitive display screen) such as that depicted in FIG. 1. Contained within the base 14 of the machine 12 is a cartridge holder mechanism (not shown). The cartridge 10 is inserted into the cartridge holder mechanism via a slot 20 that is optionally located in the front of the base 14.

By the nature of the test(s) as it (they) may, the cartridge 10 may be inserted into the machine 12 before or after said cartridge 10 is filled with a liquid sample to be tested. FIG. 1 also depicts a syringe 22 used to fill the cartridge 10 with a liquid to be tested. In some embodiments, the syringe 22 is used to fill the cartridge 10 with the liquid sample after the cartridge is inserted into the slot 20 in the base 14. Thereafter, the syringe 22 remains attached to the cartridge 10 in the manner suggested in FIG. 1. So attached, the syringe 22 can conveniently serve as a "handle" for the cartridge 10. This syringe/handle feature is very useful in performing the manual operations associated with placing the cartridge 10 in the cartridge receiving slot 20 and subsequently removing the cartridge 10 from said slot. The cartridge and its syringe/handle can be disposed of as a unit. This feature serves to protect the machine operator from inadvertent contact with the liquid being tested.

After a cartridge 10 containing a liquid sample is placed in the slot 20, the machine 12 conducts an analytical test following some predetermined procedure in accordance with the type of test desired. Such procedures are known to those skilled in the manufacture of test machines. These test results also may be compared (for example, through computer-programmed comparisons) with other programmed test information and/or with other test results. For example, the detailed test procedures taught in the U.S. Pat. No. 5,629,209 (Braun, Sr., et al.), the disclosure of which is hereby incorporated by reference in its entirety, can be carried out. Again, the machine 12 can display the results of the test on a display screen 18.

Figure 2:
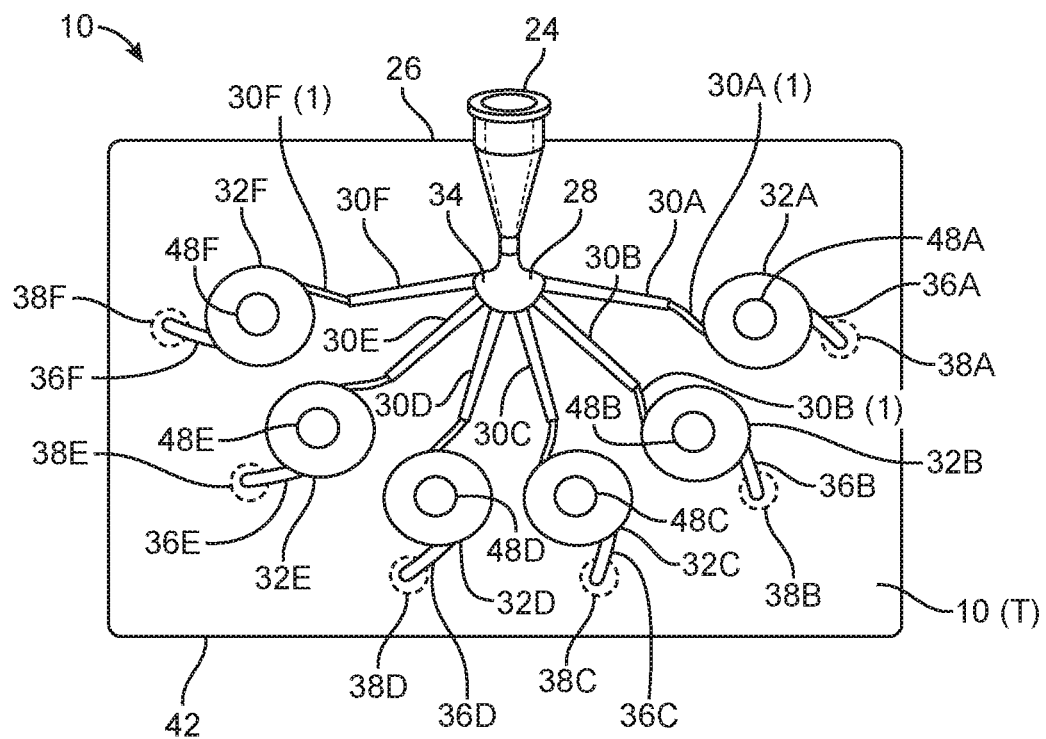
FIG. 2 is a top view of a cartridge made according to certain embodiments of this disclosure.

FIG. 2 shows a top view of one embodiment of a cartridge 10 such as that depicted in FIG. 1. The cartridge 10 is substantially planar and formed of a strong, rigid material (for example, a plastic or acrylic) that is inert with respect to the liquid/reagent sample being tested. The rigid material from which the cartridge 10 is formed may be partially or wholly transparent. The cartridge 10 may be manufactured as a unitary or monolithic piece (for example, by injection molding techniques), or it may be assembled from various separate parts. In one manufacturing method (see FIG. 3), a separate and distinct cartridge top 10(T) is attached on a cartridge bottom 10(B) after a liquid sample altering reagent (e.g., a blood viscosity-altering reagent) is placed in a conduit (e.g., conduit 30A) in the cartridge bottom 10(B). In some embodiments, the cartridge top 10(T) will be a flexible material that is used to cover the top of the fluid communication system and thereby form the top of the cartridge. This flexible material can be a polymer based, paper based material. In either case the material should be impervious to the liquid sample. In other embodiments, this flexible material will have a label-like quality in that select portions of its underside are provided with an adhesive material. The top side of this label could have printed material such as directions for using the cartridge, bar codes, words of caution, and/or technical specifications, etc. In further embodiments, the top of the cartridge will be a stiff, transparent, plastic material such as Mylar® BoPET (biaxially-oriented polyethylene terephthalate). It is to be understood, however, that various other types of plastic materials may be used for such tops 10(T) so long as they provide a fluid-impervious seal between the top 10(T) and the cartridge bottom 10(B). The cartridge bottom 10(B) can be made of compatible plastic materials that are capable of being held in an abutting relationship by a glue or adhesive material.

As shown in FIG. 2, the cartridge 10 is provided with an injection port 24 (e.g., a luer lock) that is located in a nominal rear portion 26 of the cartridge 10. A liquid sample is introduced into the cartridge 10 through this injection port 24. The injected liquid may already have been mixed with a reagent before it enters the cartridge. In certain embodiments, however, the mixing of the liquid and reagent takes place inside the cartridge 10. In any case, the injection port 24 directs the liquid sample into a fluid receiving/dispensing reservoir 28. From the fluid receiving/dispensing reservoir 28, the liquid sample proceeds through one or more fluid inlet conduits 30A, 30B, 30C . . . 30F, etc. Each such conduit respectively leads to a fluid-receiving test chamber 32A, 32B, 32C . . . 32F, etc., each having a guide post 48A, 48B, 48C . . . 48F, etc. In some embodiments, the fluid conduits have a narrow region to reduce blood flow speed, which can cause air entrapment in the fluid-receiving test chamber 32A, 32B, 32C . . . 32F, etc. The motive force for this movement of the subject liquid (e.g., blood) through the cartridge 10 is provided by a fluid injection or pumping mechanism. A manually operated syringe such as the syringe 22 shown in FIG. 1 can be used for pumping the liquid sample through the cartridge 10. In some embodiments, the conduits 30A, 30B . . . 30F are provided with a constricted portions 30A(1), 30B(1) . . . 30F(1) that angle from a direction that generally leads toward the center of the respective fluid-receiving test chambers 32A, 32B . . . 32F, to their respective wall regions.

Each fluid-receiving test chamber 32A, 32B, 32C, etc. may be equidistant from the fluid receiving/dispensing reservoir 28. Consequently the liquid sample moves from the fluid receiving/dispensing reservoir 28 simultaneously, or nearly so, into each fluid-receiving test chamber 32A, 32B, 32C, etc. In those embodiments in which the liquid sample being tested is human blood, each fluid-receiving test chamber 32A, 32B, 32C, etc. can have a volume of about 100 µl to about 250 µl. Although six fluid-receiving test chambers 32A, 32B, 32C, etc. are shown in FIG. 2, it should be understood that any desired number of fluid-receiving test chambers can be formed in the cartridge 10. Indeed, suitable cartridges could contain only one such fluid-receiving test chamber.

Figure 3:
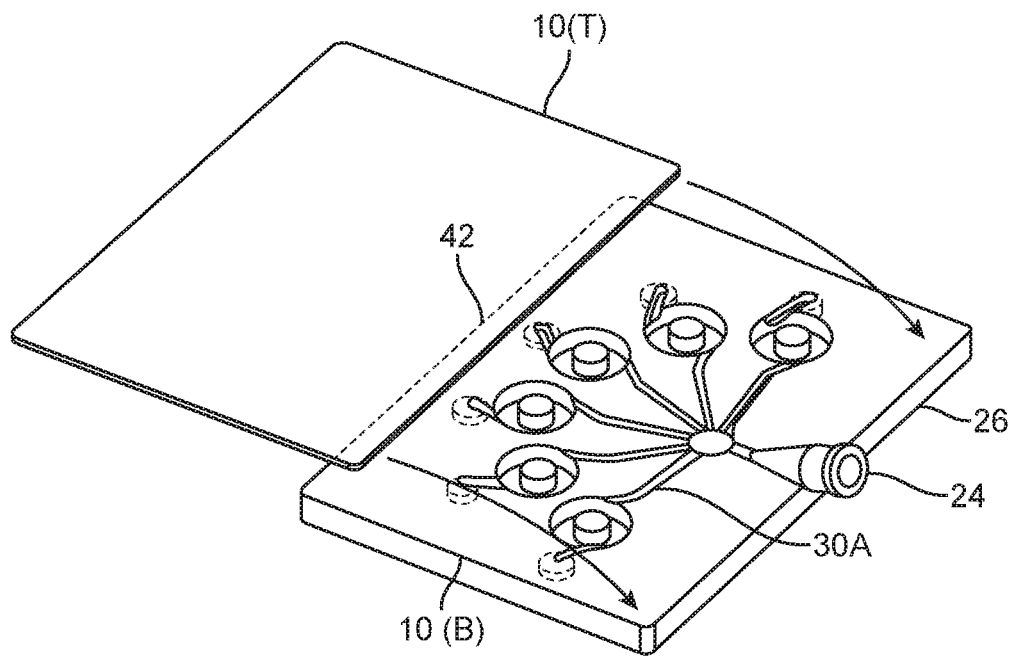
FIG. 3 is a perspective, exploded, view of the cartridge shown in FIG. 2.

Again, in various embodiments, multiple fluid-receiving test chambers 32A, 32B, 32C, etc. will be filled nearly simultaneously in order to enhance the accuracy of the analytical test results. To achieve this near-simultaneous filling, the fluid receiving/dispensing reservoir 28 can be provided with a substantially semicircular configuration so that, upon being filled, it acts as a manifold that tends to uniformly deliver the liquid sample to the fluid-receiving test chambers 32A, 32B, 32C, etc. As seen in FIGS. 3, 4 and 5, the injection port 24 enters the top 10(T) and rear 26 of the cartridge 10. It is then pressured (e.g., by a syringe) into the fluid receiving/dispensing reservoir 28. As can be better seen in FIG. 14, the conduits 30A, 30B, 30C, etc. can optionally be arrayed along the front end 34 of the fluid receiving/dispensing reservoir 28. The conduits 30A, 30B, 30C, etc. can be located closer to the top of the fluid receiving/dispensing reservoir 28 relative to location of the fluid inlet leading into the fluid receiving/dispensing test chamber 28 from the injection port 24. Thus, a fluid sample can enter a lower part of one end of the fluid receiving/dispensing reservoir 28, substantially fills the fluid receiving/dispensing reservoir 28 and then leaves said chamber 28 at a relatively higher level of the fluid receiving/dispensing reservoir 28.

Any air contained in the cartridge 10 must be vented as the liquid sample is pumped into said cartridge. To this end, each fluid receiving test chamber 32A, 32B, 32C, etc. is provided with a second conduit 36A, 36B, 36C, etc. ("fluid exit conduits") that lead from a given fluid-receiving test chamber 32A, 32B, 32C, etc. to a given air vent/fluid plug device 38A, 38B, 38C, etc. Such a vent/fluid plug is detailed in FIGS. 9 and 10. As the liquid sample enters the cartridge 10 and moves into the fluid receiving/dispensing chamber 28, air contained in the conduits 30A, 30B, 30C, etc., the fluid receiving/dispensing reservoir 28, fluid-receiving test chambers 32A, 32B, 32C, etc., the fluid exit conduits 36A, 36B, 36C, etc. and the vent/fluid plug devices 38A, 38B, 38C, etc. is driven before the incoming fluid and vented out of the cartridge 10. In some embodiments, this venting will be done through the bottom side 40 of the cartridge 10 (see FIGS. 13 and 14) via air vent/fluid plug device 38. This venting also could be done through the top 10(T) or side(s) 42 of the cartridge 10 as well. The exit conduits 36A, 36B, 36C, etc. can exit their respective fluid receiving chambers 32A, 32B, etc. at a position that is substantially opposite the position where the fluid inlet conduits 30A, 30B, etc. enter their respective fluid-receiving test chambers 32A, 32B, etc.

When the incoming liquid reaches the air vent/fluid plug device 38, a permanent liquid lock is formed. This prevents any further motion of liquid through the cartridge 10. In other words, the air vent/fluid plug device 38 allows air displaced by incoming liquid to exit the cartridge 10, but prevents liquid from leaving the cartridge 10 via said air vent/fluid plug device 38. In one embodiment, the air vent/fluid plug device 38 is formed of Porex® plastic (Porex Corp. no. X6870). This material is porous to a gas such as air, but is not porous to a liquid such as blood, and therefore acts as a liquid lock. The fluid communication system created by the fluid receiving/dispensing reservoir 28, conduit(s) 30A, 30B, etc., fluid-receiving test chamber(s) 32A, 32B, etc., and air vent/fluid plug device(s) 38A, 38B, etc. automatically places the correct amount of liquid in each fluid-receiving test chamber 32A, 32B, etc. Hence, no liquid volume measurements need to be made by human operators. This automatic measuring action provides a means whereby the volume of the fluid samples will not vary between the respective fluid-receiving chambers 32, or between tests. Fail-safe provisions also may be provided by the machine 12 to disclose incomplete filling of any fluid-receiving test chamber 32A, 32B, etc.

FIG. 3 is an exploded perspective view of the cartridge 10 shown in FIG. 3. In this disassembled state a reagent can be readily placed in one or more of the conduits (e.g., conduit 30A). In some embodiments of this disclosure, the reagent will be placed in conduit in the form of a solution or suspension. The carrier (water, alcohol, etc.) for the reagent will then be evaporated and thereby leaving behind a dried form of the reagent. The cartridge top 10(T) then can be placed on the cartridge bottom 10(B) e.g., by gluing, by an adhesive placed on the underside of a flexible, label-like cartridge top 10(T), and thereby form the unified cartridge 10 shown in FIGS. 1 and 2.

Figure 3A:
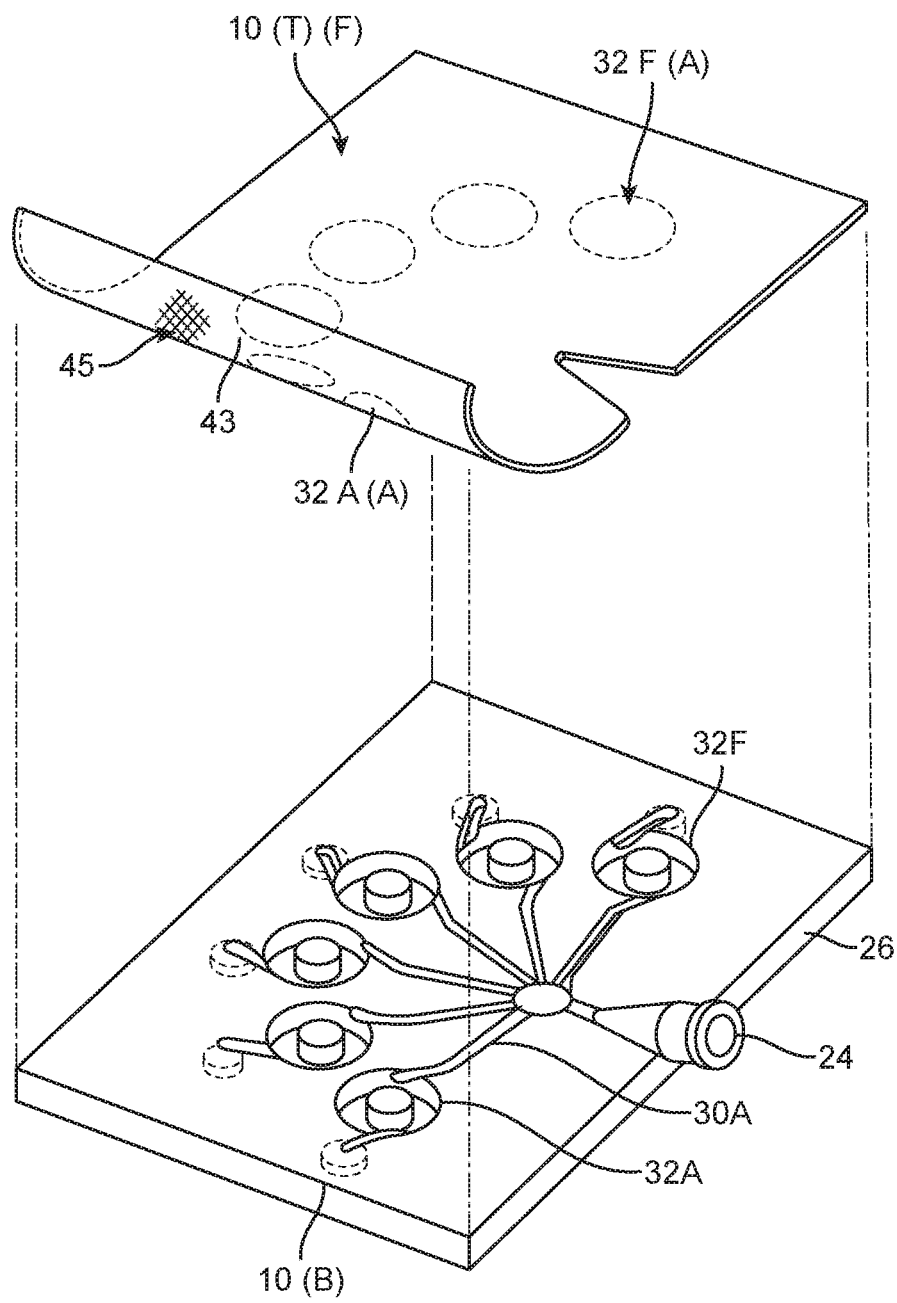
FIG. 3A is a perspective, exploded, view of the cartridge of FIG. 3 about to be provided with a flexible top.

FIG. 3A is an alternative embodiment wherein a top 10(T)(F) for the cartridge bottom 10(B) is made of a flexible material whose left end is shown curled away from a flat configuration. The underside 43 of the top 10(T)(F) is provided with regions having an adhesive material 45. The adhesive material 45 is, can be absent from those areas that cover the fluid receiving test chambers 32A . . . 32F, i.e., those round areas on the underside 43 of the top 10(T)(F) designated as 32A(A) . . . 32F(A).

FIG. 4 is a side view of the cartridge 10 shown in FIG. 2. It particularly illustrates how the injection port 24 is mounted to the top 10(T) and/or rear end 26 of the cartridge 10 at an angle beta. This angle beta can optionally be from about 30° to about 45°.

FIG. 5 is a partially cut away side view of the cartridge 10 shown in FIG. 2 having a syringe connected to the injection port 24. The syringe 22 can be used as a handle for the cartridge 10. This cut away view also suggests that a threaded nose 25 of the syringe can be threaded into a threaded injection port 24.

Figure 6:
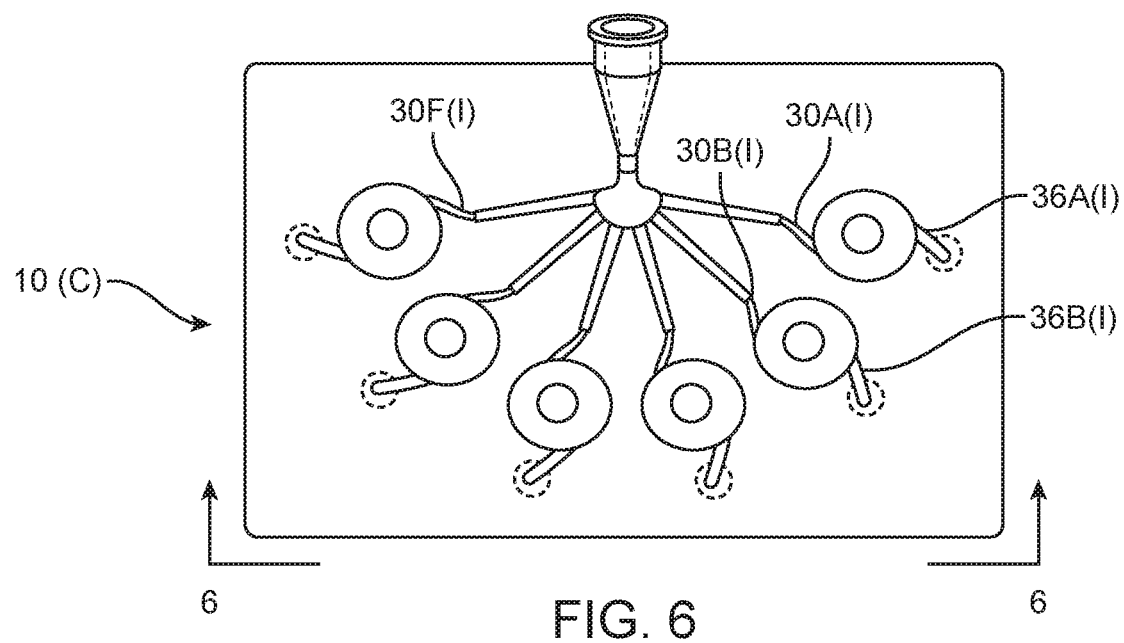
FIG. 6 is a top view of another embodiment of the cartridges of the present disclosure.

FIG. 6 depicts another embodiment wherein a cartridge 10(C) is provided with six fluid receiving test chambers.

Figure 7:
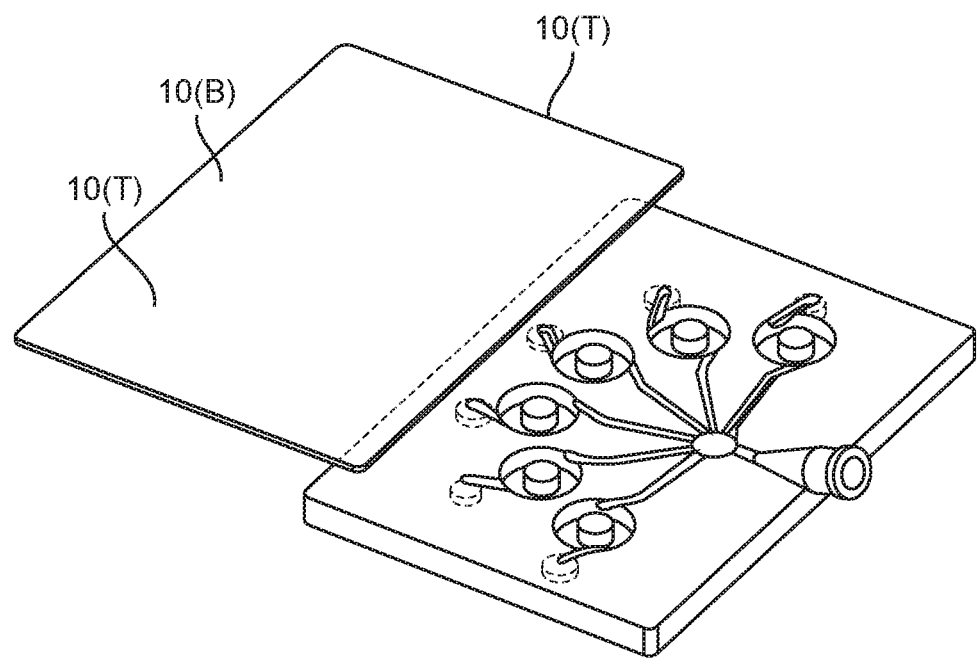
FIG. 7 is a perspective, exploded view of the cartridge shown in FIG. 6.

FIG. 7 is an exploded view of the cartridge shown in FIG. 6.

Figure 8:
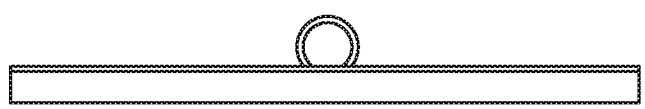
FIG. 8 is a rear view of the cartridge shown in FIG. 6.

FIG. 8 is a rear view of the cartridge 10(A) shown in FIG. 6.

Figure 9:
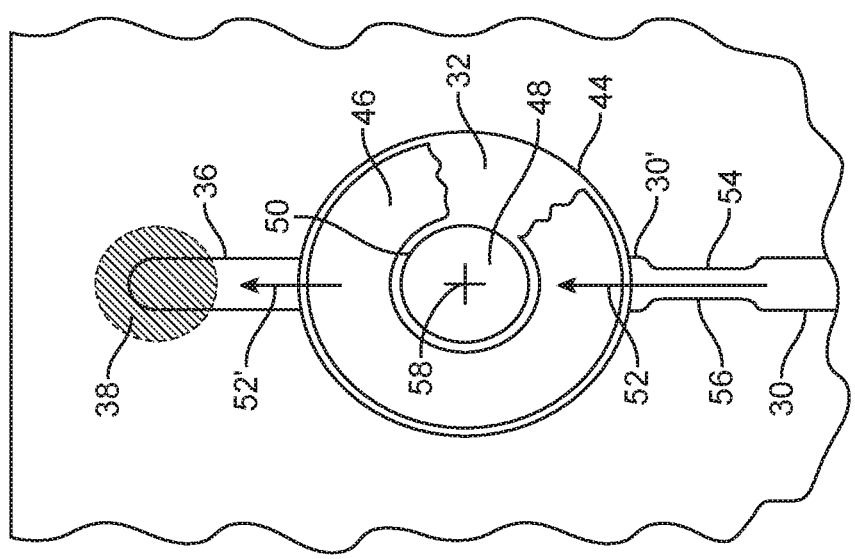
FIG. 9 is an enlarged top view of a fluid entry conduit, fluid-receiving test chamber, fluid exit conduit and vent/fluid plug device of the present disclosure.

FIG. 9 is an enlarged top view of a fluid-receiving test chamber 32 and the fluid inlet conduit 30, fluid exit conduit 36 and air vent/fluid plug 38 associated with it. It also illustrates use of the disclosed embodiments in a test wherein: movement of a ferromagnetic washer-like object 46 positioned around one respective guide post 48 of the test chamber 32 is used to detect changes in a property of the sample (e.g., the viscosity of the blood sample). In such a test, at least one, and in some embodiments each, fluid-receiving test chamber will contain such a freely movable ferromagnetic object such as the washer-like object 46 depicted in FIGS. 9, 10 and 14. When a blood viscosity analysis is performed, the ferromagnetic object 46 is raised under a magnetic action to the top of the test chamber and then is permitted to fall through the blood/reagent mixture to the bottom of the test chamber. One or more characteristics of the descent of the washer (e.g., descent time) can measured by detecting the position of the ferromagnetic object under various conditions (e.g., after repeated raising and lowering of the washer). This reciprocating motion of the ferromagnetic object is repeated until a change in fall time in one or more of the fluid-receiving test chambers signals a change in the viscosity of the blood/reagent mixture within those one or more fluid-receiving test chambers. FIG. 9 also shows that the fluid-receiving test chamber 32 can be configured to have a round external wall 44. As can be better seen in FIG. 14, the washer-like object 46 is free to vertically rise and fall inside the test chamber 32. This vertical rise and fall may be guided by a guide post 48 in the test chamber. In effect a guide post 48 may occupy the washer-like object's center hole 50.

FIG. 9 also depicts a fluid sample 52 being pumped into the fluid-receiving test chamber 32 via conduit 30. The conduit 30 is shown provided with a constricted passage 54. A reagent 56 (e.g., a dried blood viscosity changing reagent) is shown positioned in a center region of said constricted passage 54. In this view, the constricted passage flares out into a conduit section 30' having a cross section comparable to the fluid inlet conduit 30 before leading into the fluid-receiving test chamber 32. In FIG. 9, conduit 30 is shown positioned in an alternate orientation with respect to the fluid-receiving test chamber 32. That is to say that, in effect, the flow 52 of the fluid sample is aimed at the center 58 of the fluid-receiving test chamber 32. Fluid flow 52' from the fluid-receiving test chamber 32 exits said test chamber, via fluid exit conduit 36, in a similar manner. That is to say that the exit flow 52' of the fluid is through an exit conduit 36 that is essentially perpendicular to the chamber wall 44 (i.e., the fluid flow 52' from the test chamber 32 can be thought of as emanating from a region near the center 58 of said test chamber). The exit conduit 36 leads to an air vent/fluid plug device 38.

Figure 10:
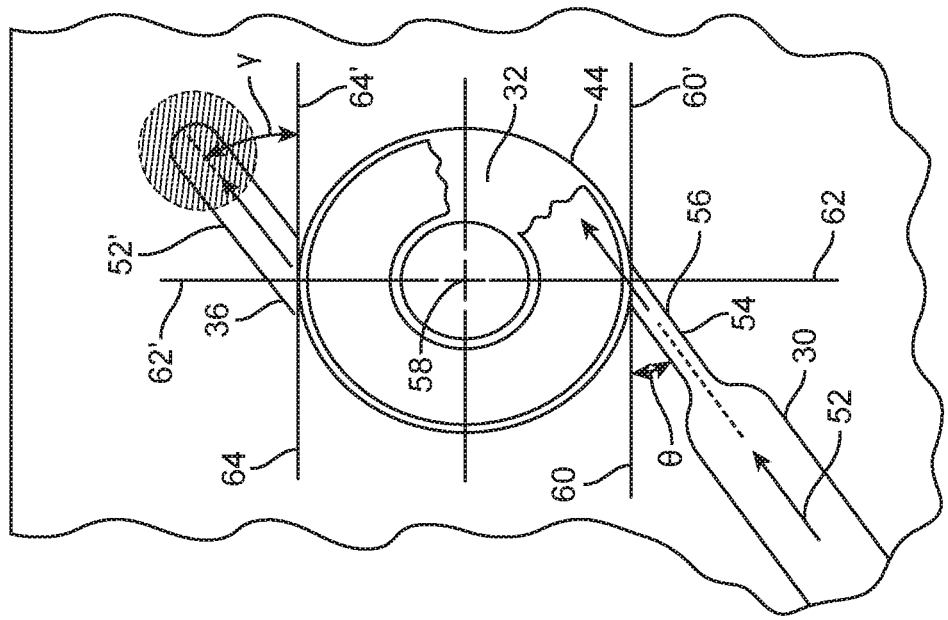
FIG. 10 is an enlarged top view of another fluid entry conduit, fluid-receiving test chamber, fluid exit conduit and vent/fluid plug device of the present disclosure.

FIG. 10 shows yet another embodiment wherein the inlet conduit 30 has a constricted passage 54 (containing a reagent 56) that leads into the fluid-receiving test chamber 32 in a substantially tangential flow pattern. That is to say that the flow of fluid 52 into the fluid-receiving test chamber 32 is directed more toward the outer wall 44 of the test chamber rather than toward the chamber's center 58 (as it is in the embodiment shown in FIG. 9). This substantially tangential flow pattern is depicted in FIG. 10 by first placing a tangent line 60/60' on the chamber wall 44 such that it is substantially perpendicular to the round chamber's center line 62/62'. The angle theta at which the constricted passage 54 approaches the wall 44 of the fluid-receiving test chamber 32 can be less than 45°. In some embodiments, the angle theta will be less than 20°; and in some embodiments this angle theta will approach the zero angle associated with tangent line 60/60'.

Figure 10A:
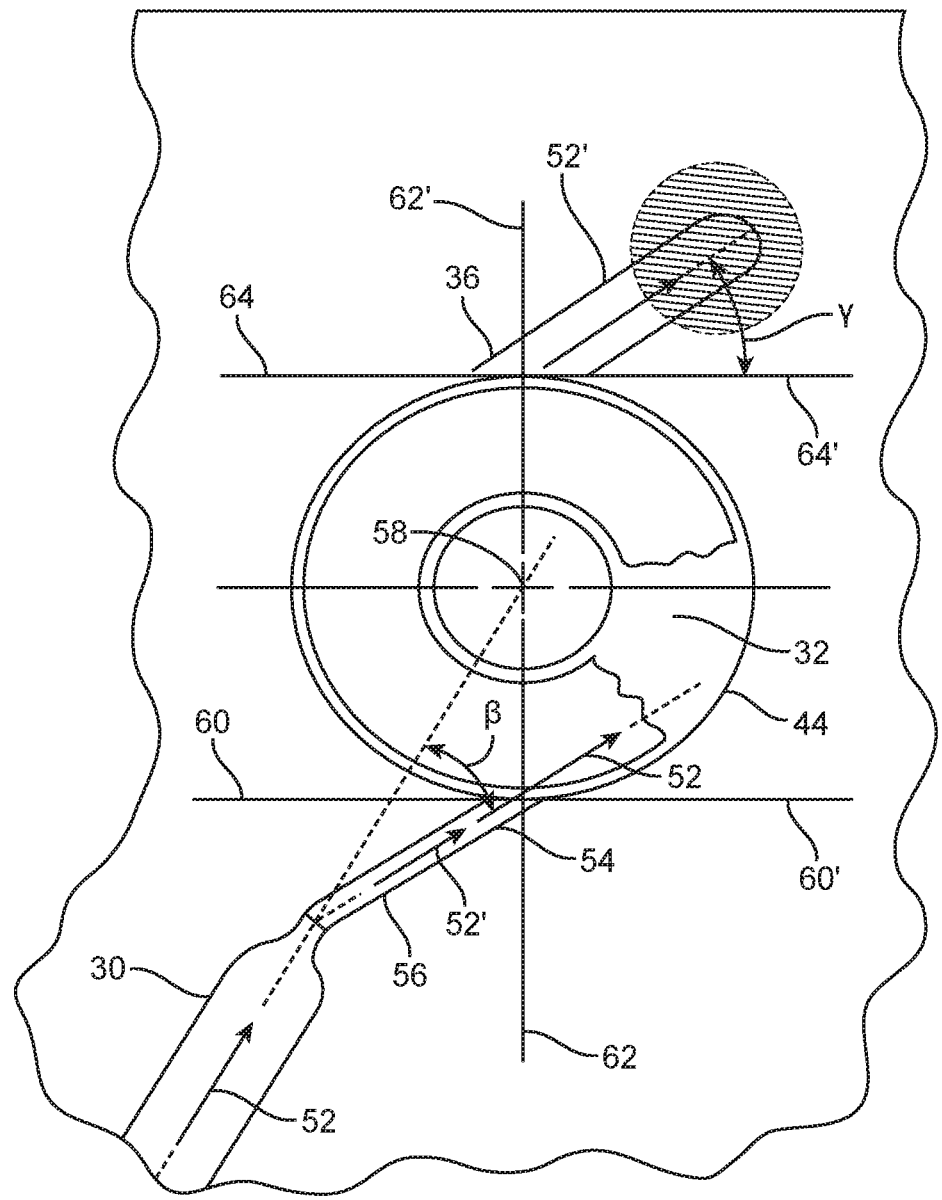
FIG. 10A is an enlarged top view of another cartridge; wherein the conduit between the fluid receiving/dispensing reservoir and the fluid-receiving test chamber has a constricted region that angles from the first part of the conduit and approaches the wall of fluid-receiving test chamber in a tangential manner.

FIG. 10A shows another embodiment wherein the inlet conduit 30 has a constricted passage 54 (containing a reagent 56) that leads into the fluid-receiving test chamber 32 in a substantially tangential flow pattern. The flow 52 through a first portion of the conduit 30 is generally aimed toward the center 58 of the fluid-receiving test chamber 32. This flow 52 is however directed into a constricted passage 54 at an angle Beta prime which is such that the flow 52 enters the fluid-receiving test chamber 32 in a tangential fashion (as opposed to being aimed at the center 58 of the fluid-receiving test chamber 32), near the perimeter or outer wall 44 of said test chamber 32. That is to say that the flow of fluid 52 into the fluid-receiving test chamber 32 is directed more toward the outer wall 44 of the test chamber rather than toward the chamber's center 58 (as it is in the embodiment shown in FIG. 9). This substantially tangential flow pattern is depicted in FIG. 10A by first placing a tangent line 60/60' on the chamber wall 44 such that it is substantially perpendicular to the round chamber's center line 62/62'. The angle Beta prime at which the constricted passage 54 approaches the wall 44 of the fluid-receiving test chamber 32 can be less than 45°. In some embodiments, the angle Beta prime will be less than 20°; and in further embodiments this angle Beta prime will approach the zero angle associated with tangent line 60/60'.

Similarly, fluid flow 52' out of the test chamber 32 leaves in a tangential flow direction as well. This circumstance is depicted in FIG. 10A by virtue of the fact that the fluid flow 52' out of the test chamber 32 follows a direction that does not pass through the center 58 of the chamber, but rather is more tangent to the round outer wall 44 of said test chamber 32. This substantially tangential flow pattern is depicted in FIG. 10A by placing a tangent line 64/64' on the chamber wall 44 such that it is substantially perpendicular to the chamber's center line 62/62'. The angle gamma at which the exit conduit 36 leaves the wall 44 of the fluid-receiving test chamber 32 is can be less than 45°. In some embodiments, the angle gamma will be less than 20°; and in other embodiments this angle gamma will approach the zero angle associated with the tangent line 64/64'.

Figure 11:
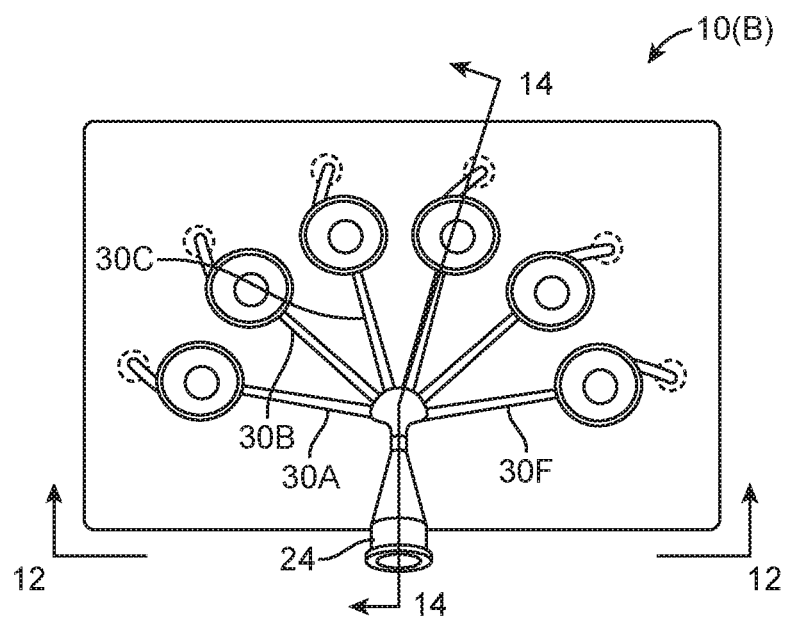
FIG. 11 is a top view of another cartridge.

FIG. 11 shows a top view of another cartridge 10(B) constructed according to the teachings of this patent disclosure. In this embodiment, the inlet conduits 30A, 30B, 30C . . . 30F are each respectively aimed at a center of a fluid-receiving test chamber 32A, 32B, 32C, etc. while the exit conduits 36A, 36B, 36C, etc. leave said test chambers in a tangential direction.

Figure 12:
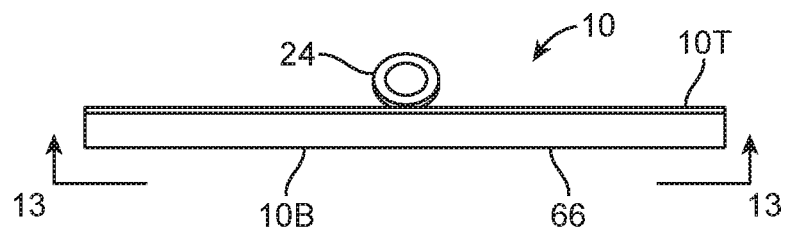
FIG. 12 is a rear view of the cartridge shown in FIG. 11.

FIG. 12 is an end view of the cartridge 10(B) shown in FIG. 11. It particularly illustrates one embodiment of the present disclosure when such a cartridge is made in two layers 10(B) and 10(T).

Figure 13:
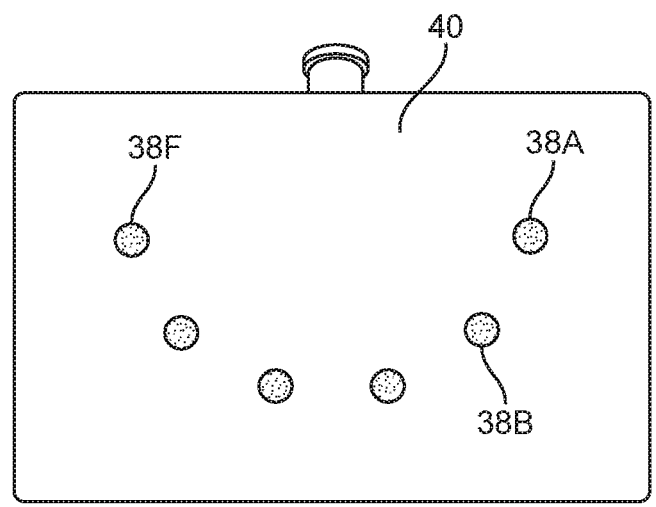
FIG. 13 is a bottom view of the cartridge shown in FIG. 11.

FIG. 13 is a bottom view of the cartridge 10(B) shown in FIG. 11. It illustrates one embodiment wherein the air vent/fluid plug devices 38 lead to the bottom side 40 of the cartridge 10(B).

Figure 14:
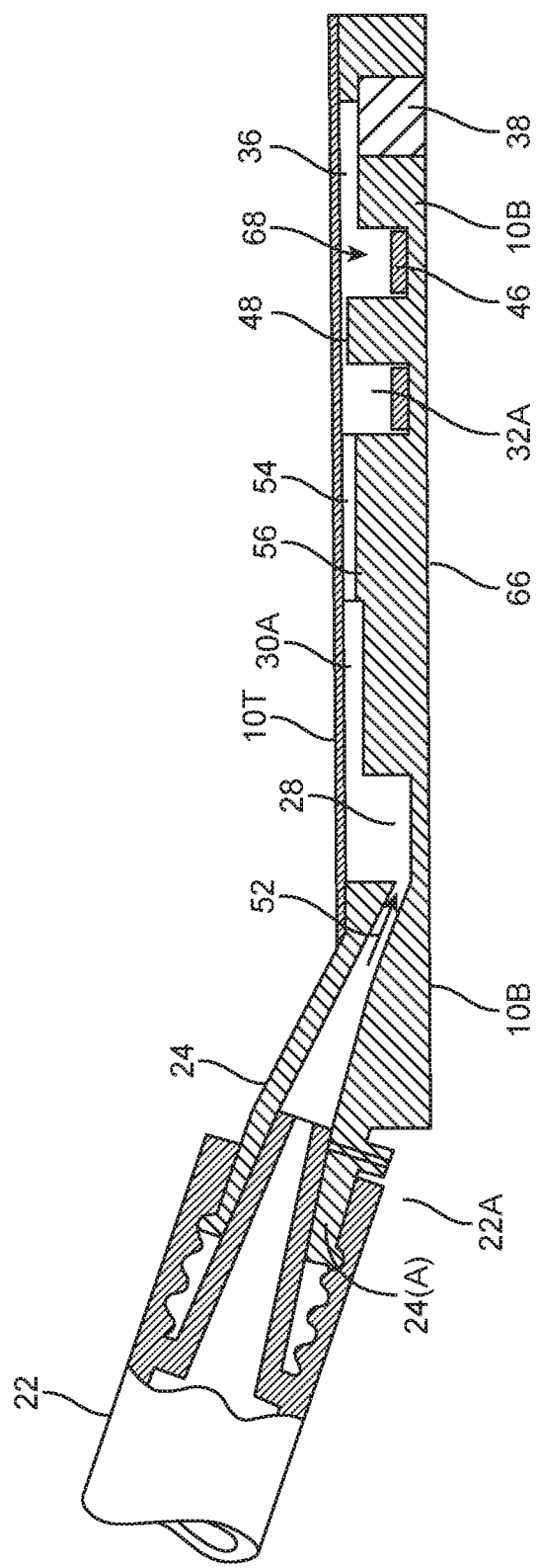
FIG. 14 is an enlarged, cut-away, cross-sectional view of the cartridge shown in FIG. 11 being used in conjunction with a syringe.

FIG. 14 is an enlarged cross sectional view of the cartridge 10(B) shown in FIG. 11 as seen along section line 14-14 thereof. A syringe 22 is depicted as being threaded into an injection port 24 in the cartridge 10(B). It could be compression fitted as well. Such a compression fit also could be augmented by use of a locking device that mechanically connects the syringe 22 to the injection port 24. For example, the locking device may be a so-called "bayonet lock" wherein a nub or other protrusion on the syringe 22 may be guided into a first keyway. Upon reaching the bottom end of such a first keyway, the syringe 22 is rotated (about 90°) and thereby forcing the protrusion into a second receiver slot or keyway that is substantially perpendicular to the path of the first keyway.

Fluid flow 52 from the syringe 22 enters the injection port 24 and flows under pressure provided by the syringe 22 to the fluid receiving/dispensing chamber 28. In this embodiment, the fluid flow 52 will enter said chamber 28 at a level that is lower than the level at which fluid leaves said chamber 28 (i.e., at the level of conduit 30A). Fluid leaving chamber 28 enters inlet conduit 30A and flows to a fluid-receiving test chamber 32. In one embodiment, the inlet conduit 30A has a constricted passage 54 (see again FIG. 10). Optionally, the reagent 56 that the liquid will be mixed with is positioned in this constricted passage 54. Dried deposits of such reagents 56 are particularly beneficial in this particular location. Upon leaving the inlet conduit 30A (or its constricted passage 54) the liquid flow enters the fluid-receiving test chamber 32A. After said test chamber 32A is substantially filled, the liquid flow enters the fluid exit conduit 36 that leads to the air vent/fluid plug device 38.

Again, this device allows air to be driven from the cartridge 10B, but prevents the liquid from leaving said cartridge via the air vent/fluid plug 38.

FIG. 14 also illustrates examples of how two distinct kinds of tests can be conducted in the cartridges of this patent disclosure. The first type of test is depicted by the penetration of a wave-like line 68 into the test chamber 32. This wave-like line is intended to depict electromagnetic energy of various kinds. Such energy can be used to detect various attributes of a liquid residing in the test chamber 32. Again a wide variety of tests for viscosity, translucence, color, electrical conductivity, optical density, chemical component concentration, etc. can be conducted by exposing the sample to various forms of electromagnetic energy. One or more different forms of electromagnetic energy 68 can be produced by a test machine such as the test machine 12 depicted in FIG. 1. One or more different forms of electromagnetic energy also can be directed at one or more test chambers 32A, 32B, 32C, etc. in a cartridge. They also can be directed at different chambers simultaneously, or they can be directed at the same test chamber (e.g., the test chamber 32A of FIG. 14) sequentially.

Again, one type of test in the practice of this disclosure involves detection of the portion of a ferromagnetic washer 46 such as that shown in FIGS. 9 and 10. Again, movement of such a washer 46 through a liquid whose viscosity changes (as a result of contact with a viscosity altering reagent) can form the basis of various tests. Once again, applicants will use movement of such a washer 46 through a blood sample as a representative use of the cartridges of this patent disclosure. In such a test, a ferromagnetic object (such as one made of iron, nickel, cobalt, and numerous alloys known to the art) can be placed in at least one of several fluid-receiving test chambers 32A, 32B, 32C, etc., in a given cartridge. Such a ferromagnetic object may act both to induce and to measure viscosity changes in the fluid. In one embodiment, this ferromagnetic object is a single piece such as a washer made of steel or other iron-based alloy. Such a washer is depicted in FIGS. 9 and 10. To ensure accurate and reliable results of the analytical tests, each such washer 46 should meet strict specifications, especially as to its physical measurements. Although the ferromagnetic object 46 used in this embodiment will normally be a steel or other iron-based alloy washer, it should be understood that other magnetically affected materials, having other physical shapes, are within the scope of the present disclosure. Hence, references herein to "washers" may include other materials and shapes. Indeed, ferromagnetic objects can be introduced to in liquid sample in the form of beads, large particles, or even filings. The essential attribute is that the ferromagnetic object be freely movable in the fluid within the fluid-receiving test chamber 32. Such a ferromagnetic object can be moved under the action of a magnet or by other means, for example, by the force of gravity. In any case, the ferromagnetic object can be configured not have a large volume relative to the volume of the fluid-receiving test chamber 38. In the context of blood testing, applicants have found that if a ferromagnetic washer 46 is employed, it can be configured to displace a volume of about 10 μl to about 50 Thus, the volume of the liquid sample that can be injected into a given fluid-receiving test chamber 32 can be about 50 μl to about 240 μl, based on a total fluid test chamber volume of about 100 μl to about 250 μl. As was previously noted, one embodiment of this disclosure employs a ferromagnetic washer 46 having a center hole in which a guide post 48 is positioned to guide the washer substantially straight up and straight down in the test chamber 32.

In a blood viscosity test, a viscosity-altering reagent can be placed within the cartridge between the injection port 24 and the fluid-receiving test chamber 32 (e.g., in the injection port itself, in the fluid receiving/dispensing reservoir or in a conduit that connects the fluid receiving/dispensing channel). Again, one desired location is in a constricted passage of a conduit located between the fluid receiving/dispensing reservoir and the fluid receiving test chamber. In the case of a heparin/protamine test, for example, a different amount of protamine, which is a heparin neutralizer, can be placed within a constricted passage of each of several conduits before a heparinized blood sample is introduced into the cartridge. The blood mixes with the protamine as it travels through a given conduit system. After the blood fills the fluid receiving test chamber(s), the test apparatus proceeds to raise the ferromagnetic object in one or more of the fluid-receiving test chambers and then repeatedly measures one or more fall characteristics (e.g., changes in fall times) of that ferromagnetic object through the blood sample. Useful inferences are then made from such fall times (relative to some standard and/or relative to fall times in different test chambers within the system). For example, the test chamber in which blood clots first is the test chamber in which the protamine level is closest to the heparin level of the blood sample.

It also should be understood that different amounts or more than one type of viscosity-altering substance may be used in each conduit 30A, 30B, 30C, etc. For example, in a heparin/protamine test of human blood, each such conduit may receive a different amount of protamine and, if desired, one or more different viscosity-altering substances (for example, a clotting activator such as tissue thromboplastin) in addition to the protamine. Those skilled in this art also will appreciate that several viscosity-altering substances can serve to decrease the tendency of blood to coagulate. They include, but are not limited to, heparin, warfarin, dicumarol, acenocoumarol, phenprocoumon, diphenadione, phenindione, sodium citrate, citric acid, citrate dextrose, citrate phosphate dextrose, aspirin, and edetate disodium. Viscosity-altering substances that act to increase the tendency of blood to coagulate include, but are not limited to, protamine, platelet-activating factor, factor VIII, factor IX complex, factor XVII, fibrinogen, aminocaproic acid, thrombin, thromboplastin, vitamin K, calcium chloride, kaolin, and diatomaceous earth.

As an example of such usage for a heparin/protamine test, in which the fluid sample to be analyzed is heparinized human blood, the viscosity-altering substance 56 will be protamine. A certain amount of protamine will neutralize the activity of an equivalent amount of heparin, thereby permitting the heparinized blood to clot. Thus, to prepare a cartridge 10 for a heparin/protamine test, a different amount of protamine can be placed in each of the conduits 30A, 30B, 30C, etc. The amount of protamine used can be chosen based on the probable amounts of heparin that exist in the blood sample. Thus, the cartridges 10 of this disclosure can be made available for a broad spectrum of surgical heparin levels. For example, when a patient is known to have a possible heparin level in his blood of between about 3 units per milliliter (ml) and 5 units per ml, in order to determine the precise amount of protamine that will be needed to neutralize the heparin in that patient's blood, the range of protamine placed into the conduits 30A, 30B, 30C, etc. may extend from less than about 3 units per ml to more than about 5 units per ml, with each conduit receiving a different amount within that range. Under such a testing strategy, the fluid-receiving test chamber 32A, 32B, 32C, etc. in which clotting is first observed is that test chamber in which the amount of protamine is closest to the amount of heparin activity in the blood that is being circulated.

Figure 15:
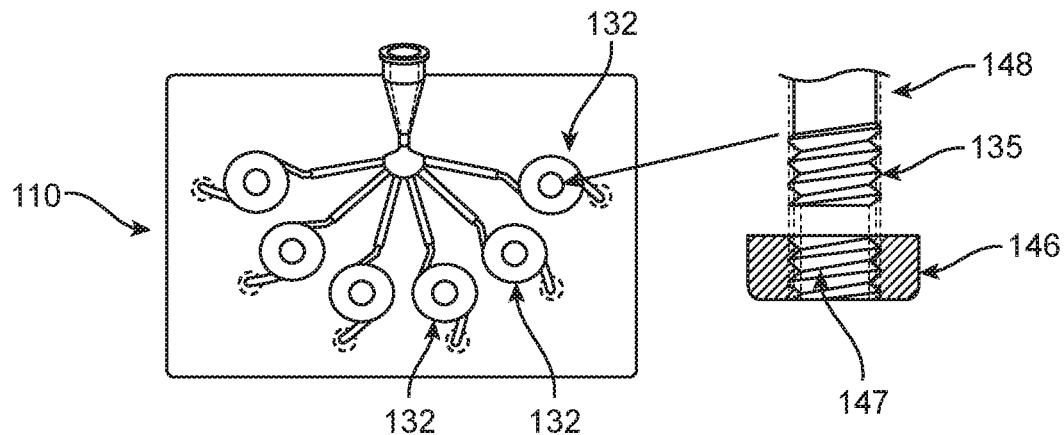
FIG. 15 is a partial, schematic illustration of another embodiment of a cartridge including at least one test chamber having a threaded guide post that can be engaged with a threaded magnetic washer.
Figures 16A, 16B:
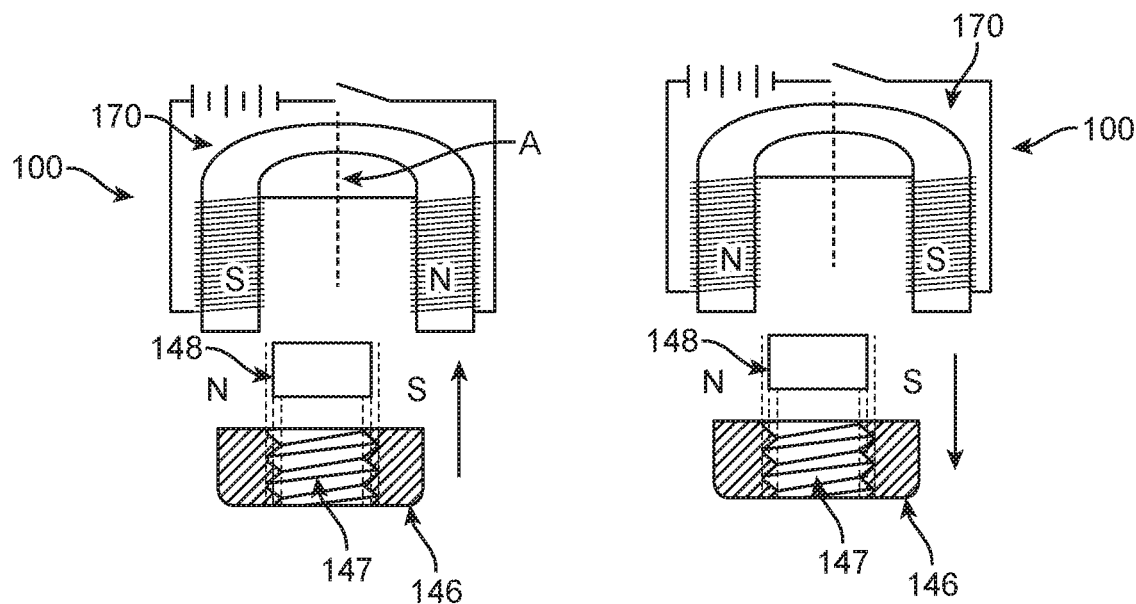
FIG. 16A is a partial, schematic illustration of a system including the cartridge of FIG. 15 (only part of which is shown) including a machine having an actuating magnet that is oriented to pull the washer in a direction of the actuating magnet.
FIG. 16B is a partial, schematic illustration of the system of FIG. 16A illustrating the actuating magnet positioned to push the washer in a direction away from the actuating magnet.

With the above general explanations of exemplary systems including machines, cartridges and methods of use, FIGS. 15-16B schematically illustrate a further embodiment of a cartridge 110 and select components of a machine or device 100 in which the cartridge 110 can be used. The machine 100 and cartridge 110 can configured similarly and used as a system as described with respect to the embodiments above except as explicitly stated. In this embodiment, the cartridge 110 includes a plurality fluid-receiving test chambers 132 (e.g., six, only a few of which are referenced), each including a guide post 148 having a threaded surface 135 that corresponds to at least one thread 147 of the magnetic washer 146, which is threadably engaged with the guide post 148. In one embodiment, the threaded surface 135 includes threads oriented at an angle less than 45 degrees. As will be understood, the at least one thread 147 of the magnetic washer 146 will be correspondingly oriented. In some embodiments, the threaded surface 135 includes threads oriented at an angle in the range of 10 to 30 degrees. Therefore, absent external restrictive forces such as a clot, the magnetic washer 146 can be rotated about the guide post 148 to translate the magnetic washer 146 up and down the guide post 148. The machine or device 100, which receives the cartridge 110, includes an actuating magnet 170 that is configured to rotate about its center axis A as to correspondingly rotate the magnetic washer 146 either up or down the guide post 148 for a variety of purposes. In an alternate embodiment, the actuating magnet 170 is an electromagnet and the polarity of the electromagnet changes as the current reverses direction every half cycle (AC voltage or current source) to apply bi-directional forces to the magnetic washer. Other types of actuating magnets are envisioned. The actuating magnet 170 can be a permanent, horseshoe magnet or can be any other magnet that can alternatingly change its poles (N, S) or the position of its poles to apply magnetic force on the poles (N, S) of the magnetic washer 146 in two directions along the guide post 148. The washer 146 can be moved up and down the guide post 148 to measure the viscosity change in a fluid sample for clotting. The distance the washer 146 moves along the guide post 148 can be measured by a proximity sensor (not shown). The position detector in one embodiment is a radio frequency detector. Radio frequency detectors sense the position of the washer 146 by sensing the changes in the magnetic field surrounding the detection coil of the radio frequency detector that are caused by the presence of the washer 146. Radio frequency detectors have sensitivity to ferromagnetic and other metallic materials and resistance to effects caused by other elements of the device, such as the fluid. It should be understood, however, that other types of position detectors are also possible. For example, in another embodiment, the position detector is a Hall effect sensor and its associated circuitry, as generally described in U.S. Pat. No. 7,775,976 (the entirety of which is incorporated by reference) at column 16, line 15 to column 17, line 5. Alternatively, the rotation of the washer 146 can be measured by a rotation or angle sensor (not shown). Clot formation is detected by the cessation of vertical washer 146 movement (i.e. rotation) with respect to the guide post 148 if sensed by a vertical position sensor or the cessation of the washer rotation with respect to the guide post 148 if sensed by a rotation or angle sensor.

Figure 17A:
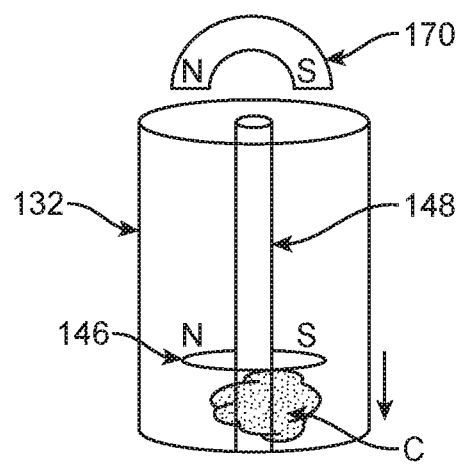
FIG. 17A is a partial, schematic illustration of the actuating magnet of FIGS. 16A-16B oriented to push the washer toward a floor of the test chamber to compress a clot formed below the washer (the non-clotted portion of the fluid sample is not shown for clarity).
Figure 17B:
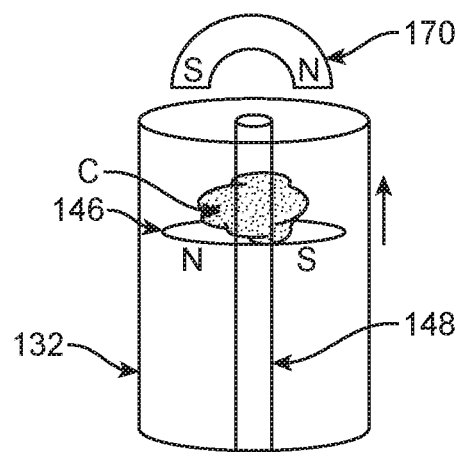
FIG. 17B is a partial, schematic illustration of the actuating magnet of FIGS. 16A-16B oriented to pull the washer toward a ceiling of the test chamber to compress a clot formed above the washer (the non-clotted portion of the fluid sample is not shown for clarity).
Figure 17C:
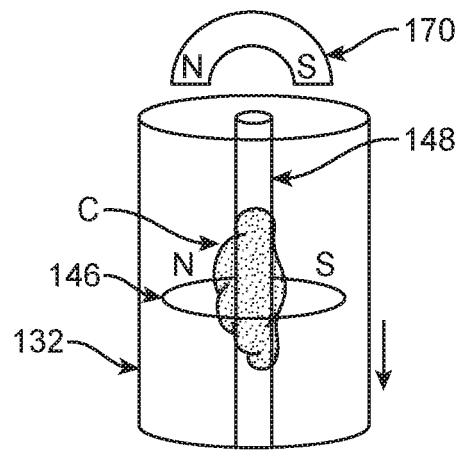
FIG. 17C is a partial, schematic illustration of the actuating magnet of FIGS. 16A-16C oriented to push the washer toward the floor of the test chamber to stretch a clot formed within the washer (the non-clotted portion of the fluid sample is not shown for clarity).
Figure 18A:
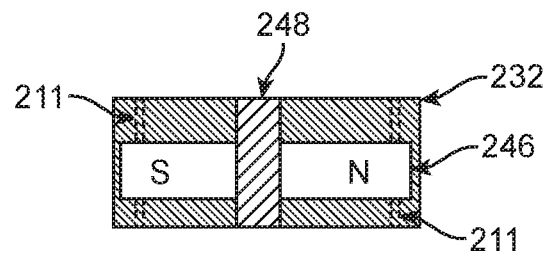
FIG. 18A is a partial, schematic cross-sectional view of an alternate embodiment including a test chamber having a magnetic washer positioned over a guide post.
Figure 18B:
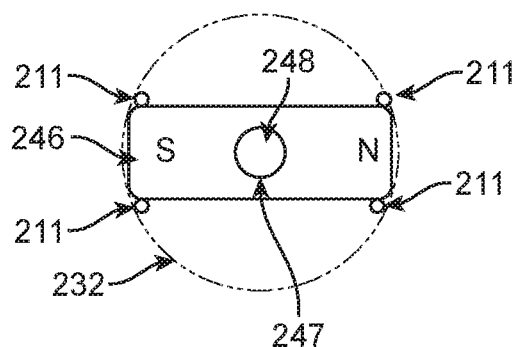
FIG. 18B is a top view of the test chamber of FIG. 17A.

In addition, the washer 146 can be moved in either direction along the guide post 148 after clot formation to assess elastic properties of the clot or firmness of a formed clot C as schematically depicted in FIGS. 17A-17C (a non-clotted portion of the fluid sample is not shown for ease of illustration). In this embodiment, the stress force in the strain-stress elasticity measurement is again controlled via the actuating magnet 170. In this way, the strain (compression or stretching) of the clot C can be controlled. Although the initial location of the washer 146 at the time of clot formation is not controlled, the distance the washer 146 can be moved up or down can be controlled with the actuating magnet 170. Therefore, strain and stress forces on the clot C can be controlled in the system and the elasticity of the clot C can be reproducibly measured. In the case where the clot C is formed under (FIG. 17A) or on top (FIG. 17B) of the washer 146, force can be applied to the washer 146 by orienting the poles (N, S) of the actuating magnet 170 accordingly to compress the clot C either against the floor or ceiling of the test chamber 132, respectively. If the clot C forms within the washer 146, the washer 146 can be pulled either upward or downward (FIG. 17C) along the guide post 148 with the actuating magnet 170 to apply a stretching force within the clot C. Both compression and stretch forces can be assessed to determine elastic properties of the clot C.

Figures 19A, 19B:
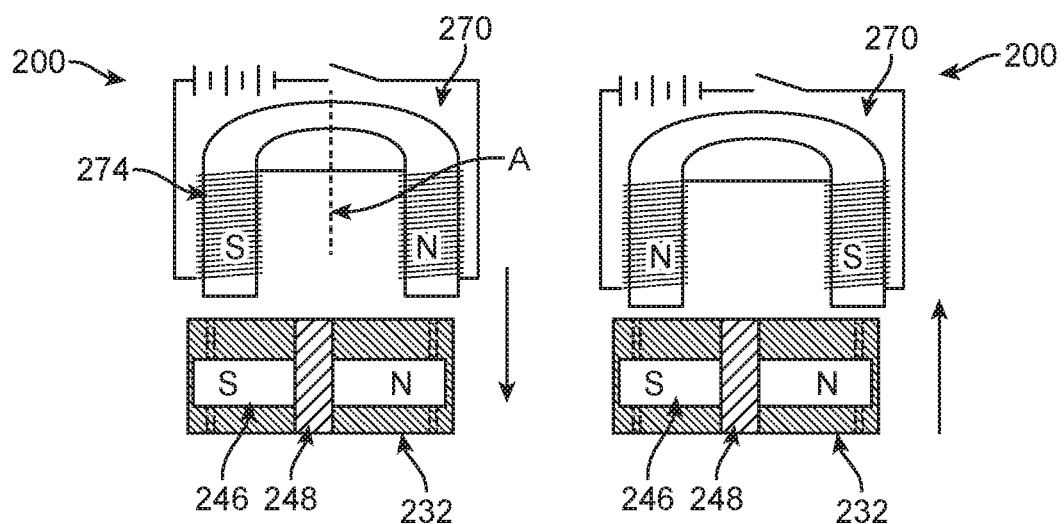
FIG. 19A is a partial, schematic illustration of a system including a cartridge (only part of which is shown) including one or more test chambers of the type of FIGS. 17A-17B showing the actuating magnet positioned to push the washer in a direction away from the actuating magnet.
FIG. 19B is a partial, schematic illustration of the system of FIG. 18A illustrating the actuating magnet positioned to pull the washer in a direction toward the actuating magnet.

Referring now also to FIGS. 18A-19B, which schematically illustrate one representative test chamber 232 which can be incorporated into a cartridge for use with a machine or device 200 (partially shown). The cartridge (not shown) and the machine 200 can be configured similar to and operate as described with respect to the cartridges and machines disclosed above except as explicitly stated. As with prior embodiments, the cartridge includes a plurality fluid-receiving test chambers 232, each having a guide post or vane 248 and a magnetic washer or bar magnet 246 having an aperture 247 through which the guide post 248 is inserted. The bar magnet 246 can have a length that is substantially the same as an internal diameter of the fluid-receiving test chamber 232. Only one fluid-receiving test chamber 232 is illustrated, however, it will be understood that the other fluid-receiving test chambers of a cartridge can optionally be similarly configured so that all test chambers are identical. The bar magnet 246 is configured to slide up and down the guide post 248 as controlled by an actuating magnet 270 provided as part of the machine or device 200 which can otherwise be of the type machines disclosed above with respect to prior embodiments. When the poles (N, S) of the actuating magnet 270 and the bar magnet 246 are similarly aligned, the bar magnet 246 slides down the guide post 248 in a direction away from the actuating magnet 270 (FIG. 19A). When the poles (N, S) of the actuating magnet 270 and the bar magnet 246 are oppositely aligned, the magnet force is such that the bar magnet 246 will generally slide upward and will be drawn toward the actuating magnet 270 (FIG. 19B). As indicated above, changes in the fluid viscosity of the fluid sample within the test chamber 232 may restrict movement of the bar magnet 246, thus indicating the formation of a clot. In one embodiment, the actuating magnet 270 is a permanent magnet that is a horseshoe magnet, which is configured in the machine 200 to rotate about its center axis A. The distance the bar magnet 246 moves along the guide post 248 can be measured by a proximity sensor (not shown, see also the above disclosure with respect to prior embodiments). Clot formation is detected by the cessation of vertical movement of the bar magnet 246 with respect to the vane 248. To prevent the bar magnet 246 from rotating about the vane 248, the cartridge 210 can optionally include a plurality of rails 211 or the like positioned within the chamber 232. In one example, the rails 211 extend along a height of the chamber 232 at each of four corners of the bar magnet 246. Other ways of restricting rotational movement of the bar magnet 246 are envisioned.

Elastic properties of a formed clot (not shown) can be assessed in similar ways to that disclosed above with respect to the embodiment of FIG. 15-17C by either moving the washer 246 either up or down along the guide post 248 to place compressive or stretching forces on the clot and further measuring a position of the washer 246 with the proximity sensor (not shown).

Although the present disclosure has been described with reference to preferred embodiments, workers skilled in the art will recognize that changes can be made in form and detail without departing from the spirit and scope of the present disclosure.

What is claimed is:

1. An apparatus configured to analyze a fluid sample, comprising:
   a cartridge including a chamber having a post and a magnetic washer engaged with the post; and
   an actuating magnet positioned proximate the chamber; wherein the actuating magnet is configured to apply force on the magnetic washer in two directions; wherein the magnetic washer is threadably engaged with the post with threads.

2. The apparatus of claim 1, wherein the actuating magnet is an electromagnet.

3. The apparatus of claim 1, wherein the magnetic washer is a bar magnet.

4. The apparatus of claim 3, wherein the chamber includes a plurality of rails that restrict rotation of the bar magnet.

5. The apparatus of claim 4, wherein the chamber includes four rails positioned on an interior surface of the chamber surrounding the bar magnet.

6. The apparatus of claim 1, wherein both of the two directions are parallel to the post.

7. The apparatus of claim 1, wherein the magnetic washer has a length that is substantially the same as an internal diameter of the chamber.

* * * * *